United States Patent
Lim et al.

(10) Patent No.: US 11,383,096 B2
(45) Date of Patent: Jul. 12, 2022

(54) SKIN CARE DEVICE

(71) Applicant: LG ELECTRONICS INC., Seoul (KR)

(72) Inventors: Gueisam Lim, Seoul (KR); Munseong Kang, Seoul (KR); Nayoung Kim, Seoul (KR); Namjin Kim, Seoul (KR); Heejung Kim, Seoul (KR); Yoonyoung Chang, Seoul (KR); Jiyoung Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 628 days.

(21) Appl. No.: 16/339,221

(22) PCT Filed: Mar. 16, 2017

(86) PCT No.: PCT/KR2017/002850
§ 371 (c)(1),
(2) Date: Apr. 3, 2019

(87) PCT Pub. No.: WO2018/066778
PCT Pub. Date: Apr. 12, 2018

(65) Prior Publication Data
US 2020/0046999 A1    Feb. 13, 2020

(30) Foreign Application Priority Data

Oct. 6, 2016    (KR) .......................... 10-2016-0128990

(51) Int. Cl.
*A61N 5/06*    (2006.01)
*A61B 5/0531*    (2021.01)
*A61F 7/00*    (2006.01)

(52) U.S. Cl.
CPC .......... *A61N 5/0616* (2013.01); *A61B 5/0531* (2013.01); *A61F 7/007* (2013.01);
(Continued)

(58) Field of Classification Search
CPC .......... A61N 5/0616; A61N 2005/0659; A61N 2005/0663; A61N 2005/0644;
(Continued)

(56) References Cited

U.S. PATENT DOCUMENTS

2006/0074468 A1* 4/2006 Neev .................... A61B 18/203
607/90
2010/0196343 A1* 8/2010 O'Neil .................... A61K 8/66
424/94.4
(Continued)

FOREIGN PATENT DOCUMENTS

BR    PI0713109 A2 * 10/2012 .......... A61B 18/203
JP    2009-28267 A    2/2009
(Continued)

*Primary Examiner* — Joseph M Dietrich
*Assistant Examiner* — Michael T. Holtzclaw
(74) *Attorney, Agent, or Firm* — Birch, Stewart, Kolasch & Birch, LLP

(57) ABSTRACT

The present invention provides a skin care device which performs optical care and thermal care in one device and minimizes noise that may occur in the skin measurement sensor, the device comprising: a housing for forming an outer appearance; a heat transfer bracket disposed at one end of the housing; a light source unit mounted on one end of the housing; a light transfer bracket including a light permeable material and fixed to the housing to cover the light source unit; a skin measurement sensor extending through a first hole formed in the light transfer bracket to protrude outward; and a first substrate mounted with the light source unit and spaced from the skin measurement sensor.

13 Claims, 11 Drawing Sheets

(52) U.S. Cl.
CPC ............... *A61F 2007/0052* (2013.01); *A61F 2007/0087* (2013.01); *A61F 2007/0088* (2013.01); *A61N 2005/0659* (2013.01); *A61N 2005/0663* (2013.01)

(58) Field of Classification Search
CPC .......... A61N 5/0625; A61N 2005/0626; A61N 2005/0632; A61N 2005/0662; A61B 5/0531; A61B 5/0022; A61B 5/442; A61B 5/4836; A61B 2562/0219; A61B 2562/0233; A61B 2562/0257; A61B 2562/0271; A61B 5/0077; A61B 5/01; A61B 5/053; A61B 5/441; A61F 7/007; A61F 2007/0052; A61F 2007/0087; A61F 2007/0088
See application file for complete search history.

(56) References Cited

U.S. PATENT DOCUMENTS

| | | | |
|---|---|---|---|
| 2012/0022618 A1* | 1/2012 | Lum | ............... A61N 5/0603 607/90 |
| 2015/0112411 A1* | 4/2015 | Beckman | ............ A61N 5/0616 607/90 |

FOREIGN PATENT DOCUMENTS

| | | | | |
|---|---|---|---|---|
| KR | | 20-0397736 Y1 | 10/2005 | |
| KR | | 100787874 B1 * | 12/2007 | |
| KR | | 10-1392417 B1 | 5/2014 | |
| KR | | 101504885 B1 * | 3/2015 | |
| KR | 10-2015-0129971 A | | 11/2015 | |
| KR | 10-2016-0026234 A | | 3/2016 | |
| WO | WO-2017069509 A1 * | | 4/2017 | ............. A61H 39/06 |

* cited by examiner (a)

(b)

(c)

(d)

(a)

(b)

(a)

(b)

SKIN CARE DEVICE

CROSS REFERENCE TO RELATED APPLICATIONS

This application is the National Phase of PCT International Application No. PCT/KR2017/002850, filed on Mar. 16, 2017, which claims priority under 35 U.S.C. 119(a) to Patent Application No. 10-2016-0128990, filed in the Republic of Korea on Oct. 6, 2016, all of which are hereby expressly incorporated by reference into the present application.

TECHNICAL FIELD

The present invention relates to a skin care device provided in further consideration of user's convenience.

BACKGROUND ART

Devices for skin care or treatment are implemented in a variety of ways. The skin is subjected to minute stimuli to change the activity of cells, which can lead to improved skin effects on wrinkles, whitening, etc.

One of the most representative forms is the noninvasive form of giving electrical impulses to the skin, or the invasive form of giving physical stimuli.

Although a device of an individually portable type was not available conventionally, as the development of wireless communication and the downsizing of components have become more common in recent years, portable care devices are popularly commercialized.

Regarding examples of ways to care for skin through electrical stimulation, there are ways of giving electrical impulses of high frequency bands, an optical way of giving stimulation of visible light areas, and a thermal way of transferring thermal energy to give simulation, etc.

However, conventional skin care devices generally have one effect per device in their care, i.e., in the way they stimulate the skin. This is because if multiple functions are implemented in a single device, there is a problem of mutual interference or the heating that occurs in a small space.

Heat problems with skin care devices can cause skin damage beyond the user's stimulation for skin care. Thus, a structure that can accurately sense the temperature of the skin in real time is required.

Nevertheless, in the related art, it was difficult to measure the correct skin condition as a BIA sensor for determining the condition of the skin or a temperature sensor for measuring the temperature causes noise due to the influence of other configurations.

DISCLOSURE OF THE INVENTION

Technical Task

To solve the aforementioned problems, the technical task of the present invention is to solve a problem that a single device is incapable of performing various kinds of skin cares and a problem that a skin condition measurement through a sensor cannot be performed accurately due to other factors.

Technical Solutions

In one technical aspect of the present invention, provided herein is a skin care device, including a housing forming an exterior, a heat transfer bracket provided to one end of the housing, a light source unit installed at the one end of the housing, a light transfer bracket including a light-transmissive material, the light transfer bracket covering the light source unit by being fixed to the housing, a skin measurement sensor externally projected by passing through a first hole formed in the light transfer bracket, and a first board having the light source unit mounted thereon, the first board spaced apart from the skin measurement sensor.

In another technical aspect of the present invention, the skin measurement sensor includes a Bioelectric Impedance Analysis (BIA) sensor.

In another technical aspect of the present invention, the skin care device further includes a connection wire electrically connected to the skin measurement sensor and the first board through a second hole formed in the first board.

In another technical aspect of the present invention, the skin care device further includes g a second board provided under the first board, and the skin measurement sensor is mounted on the second board by passing through a second hole formed in the first board.

In another technical aspect of the present invention, the skin care device further includes a conductive heat radiation contact portion provided to both sides of the first board and a heat radiation part including a heat radiation plate inclined to the first board and a heat radiation terminal coming in contact with the heat radiation contact portion by diverging from the heat radiation plate.

In another technical aspect of the present invention, the light source unit includes a first light source unit corresponding to a red visible light range and the heat radiation contact portion is provided to an area corresponding to the first light source unit.

In another technical aspect of the present invention, the heat transfer bracket forms a rim area of the one end of the housing and the light transfer bracket is formed in an inside area of the heat transfer bracket.

In another technical aspect of the present invention, a comb pattern is formed on an inner lateral side of the light transfer bracket.

In another technical aspect of the present invention, the light source unit includes 4 first light source units corresponding to a red visible light range and 8 second light source units corresponding to a near-infrared range, the 4 first light source units are arranged in a circular form on the first board, and every 2 of the 8 second light source units are arranged in each space between the first light source units along the circular form.

In another technical aspect of the present invention, the skin care device further includes a controller controlling voltage to be applied to the first light source unit and the second light source unit selectively or simultaneously.

Advantageous Effects

A skin care device according to the present invention is described as follows.

According to at least one of embodiments of the present invention, an optical care and a thermal care can be advantageously performed with a single device.

According to at least one of embodiments of the present invention, noise possibly generated from a skin measurement sensor can be advantageously minimized.

According to at least one of embodiments of the present invention, light projection efficiency by a light source unit can be advantageously maximized and a device damage due to heat generation can be advantageously minimized.

According to at least one of embodiments of the present invention, the projected light can be spread to a wide area advantageously.

Other objects and further scope of applicability of the present disclosure will become apparent from the detailed description given below. It is to be understood, however, that the detailed description and specific examples such as preferred embodiments of the disclosure are given by way of illustration only, since it is obvious to those skilled in the art that various changes and modifications can be made within the spirit and scope of the disclosure.

BEST MODE FOR INVENTION

Figure 1:
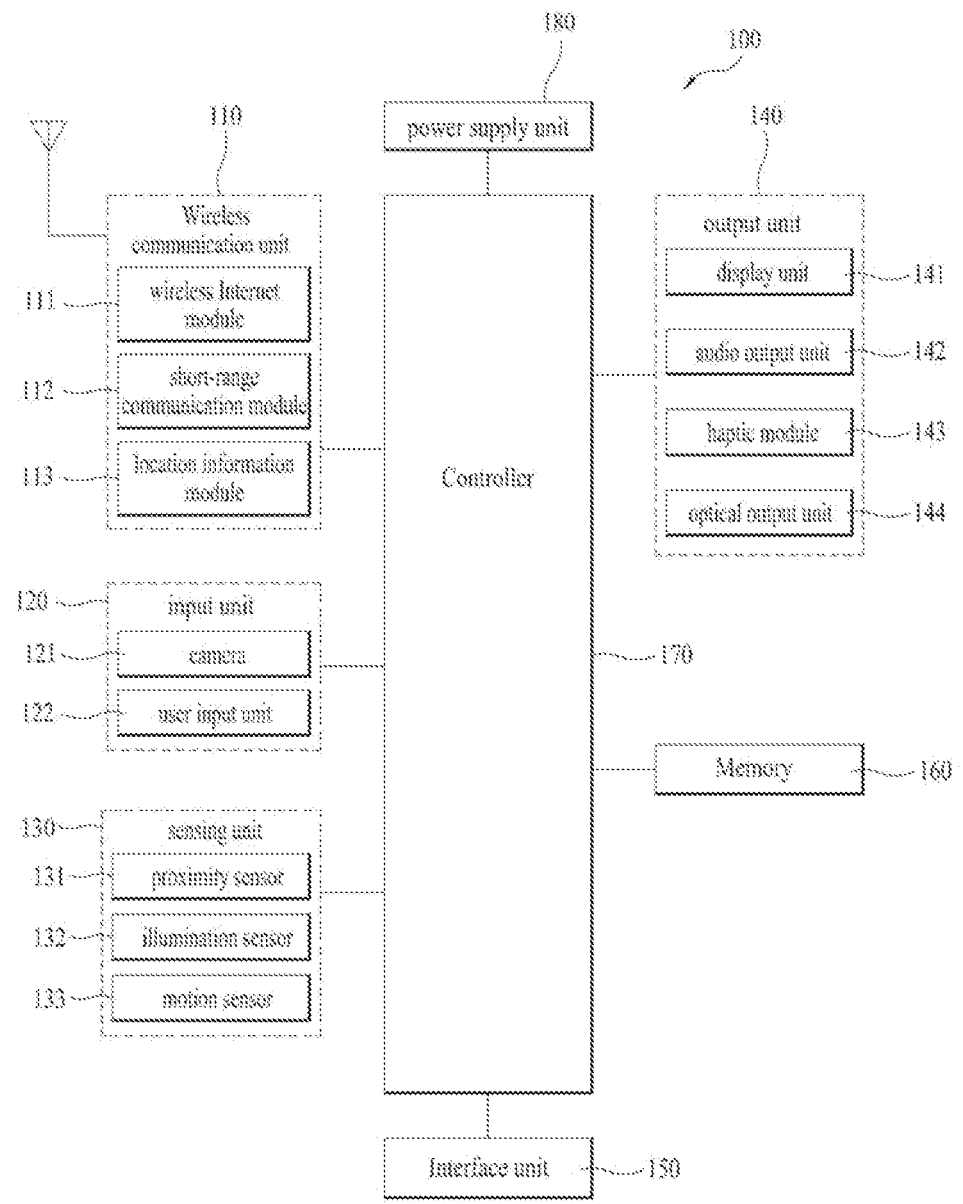
FIG. 1 is a block diagram to describe a skin care device related to the present invention.

Reference will now be made in detail to the preferred embodiments of the present invention, examples of which are illustrated in the accompanying drawings. Wherever possible, the same reference numbers will be used throughout the drawings to refer to the same or like parts. As used herein, the suffixes "module" and "unit" are added or used interchangeably simply to facilitate preparation of this specification and are not intended to suggest unique meanings or functions. In describing embodiments disclosed in this specification, relevant well-known technologies may not be described in detail in order not to obscure the subject matter of the present invention. In addition, the accompanying drawings are merely intended to facilitate understanding of the embodiments disclosed in this specification and not to restrict the technical spirit of the present invention. In addition, the accompanying drawings should be understood as covering all equivalents or substitutions within the scope of the present invention.

Terms including ordinal numbers such as first, second, etc. may be used to explain various elements. However, it will be appreciated that the elements are not limited to such terms. These terms are merely used to distinguish one element from another.

When one constituent is said to be "connected" or "linked" to another, it should be understood that this means that the one constituent may be directly connected or linked to another one or another constituent may be interposed between the constituents. On the other hand, when one constituent is said to be "directly connected" or "directly linked" to another, it should be understood that this means no other constituent is interposed between the constituents.

Singular nouns encompass the plural forms thereof unless context clearly indicates otherwise.

Terms used in this specification are merely adopted to explain specific embodiments, and are not intended to limit the present invention. A singular expression includes a plural expression unless the two expressions are contextually different from each other. In this specification, terms such as "includes" or "has" are intended to indicate that characteristics, figures, steps, operations, constituents, and components disclosed in the specification or combinations thereof exist. The terms "includes" or "has" should be understood as not precluding possibility of existence or addition of one or more other characteristics, figures, steps, operations, constituents, components, or combinations thereof.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Devices for skin care or treatment are implemented in a variety of ways. The skin is subjected to minute stimuli to change the activity of cells, which can lead to improved skin effects on wrinkles, whitening, etc.

One of the most representative forms is the noninvasive form of giving electrical impulses to the skin, or the invasive form of giving physical stimuli.

Although a device of an individually portable type was not available conventionally, as the development of wireless communication and the downsizing of components have become more common in recent years, portable care devices are popularly commercialized.

Regarding examples of ways to care for skin through electrical stimulation, there are a way of giving electrical impulses of high frequency bands, an optical way of giving stimulation of visible light areas, and a thermal way of transferring thermal energy to give simulation, etc.

However, conventional skin care devices generally have one effect per device in their care, i.e., in the way they stimulate the skin. This is because if multiple functions are implemented in a single device, there is a problem of mutual interference or the heating that occurs in a small space.

Heat problems with skin care devices can cause skin damage beyond the user's stimulation for skin care. Thus, a structure that can accurately sense the temperature of the skin in real time is required.

Nevertheless, in the related art, it was difficult to measure the correct skin condition as a BIA sensor for determining the condition of the skin or a temperature sensor for measuring the temperature causes noise due to the influence of other configurations.

FIG. 1 is a block diagram to describe a skin care device 100 related to the present invention.

The skin care device 100 may include a wireless communication unit 110, an input unit 120, a sensing unit 130, an output unit 140, an interface unit 150, a memory 160, a controller 170, a power supply unit 180 and the like.

As the components shown in FIG. 1 are not mandatory for the implementation of the skin care device, the skin care device mentioned in the present specification may have components more or less than the above-listed components.

Particularly, the wireless communication unit 100 among the components may include at least one module capable of enabling a wireless communication between the skin care device 100 and a wireless communication system, between the skin care device 100 and another external terminal, or between the skin care device 100 and an external server. And, the wireless communication unit 110 may include at least one module configured to connect the skin care device 100 to one or more networks.

The wireless communication unit 110 may include at least one of a wireless internet module 111, a short range communication module 112, and a location information module 113.

The short-range communication module 112 is configured to support short-range communications using at least one of Bluetooth™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 112 can support wireless communications between the skin care device 100 and a wireless communication system, communications between the skin care device 100 and another skin care device 100, or communications between the skin care device and a network on which another skin care device 100 (or an external server) is located, via wireless area networks. The wireless area networks may include wireless personal area networks.

Here, another external device may include a mobile terminal or wearable device (e.g., a smart watch, a smart glass, a Head Mounted Display (HMD), etc.) capable of exchanging data with (or cooperating with) the skin care device 100. The short-range communication module 112 may sense or recognize the mobile terminal or wearable device around the skin care device 100, and permit communication between the mobile terminal or wearable device and the skin care device 100. In addition, when the sensed mobile terminal or wearable device is a device which is authenticated to communicate with the skin care device 100, the controller 170 may cause transmission of at least one portion of data processed in the skin care device 100 to the mobile terminal or wearable device via the short-range communication module 112. Hence, a user of the mobile terminal or wearable device may use the data processed in the skin care device 100 on the mobile terminal or wearable device. And, the skin care device 100 may perform a specific operation by receiving data processed through the mobile terminal or wearable device.

For example, it is able to control the skin care device to be driven by transmitting data of a skin condition measured by the skin care device 100 to the mobile terminal or wearable device, obtaining the tendency of a skin condition change by establishing database of the data, and then sending feedback on the basis of the obtained tendency.

Particularly, to the skin care device 100 according to the present invention, short-range communication technologies such as Bluetooth™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus) and the like are applicable.

Among them, an NFC module provided to the skin care device 100 supports terminal-to-terminal non-contact short-range wireless communication in a distance of about 10 cm. The NFC module may operate in one of a card mode, a reader mode and a P2P mode. In order for the NFC module to operate in card mode, the skin care device 100 may further include a security module for storing card information. Here, the security module may include a physical medium such as Universal Integrated Circuit Card (UICC) (e.g., Subscriber Identification Module (SIM), Universal SIM (USIM), etc.), Secure micro SD, sticker, or the like, or a logical medium (e.g., embedded Secure Element (SE)) embedded in the skin care device. Between the NFC module and the security module, data exchange based on Single Wire Protocol (SWP) may be performed.

In case that the NFC module operates in card module, the skin care device 100 may externally forward card information stored therein like a traditional IC card.

In case that the NFC module operates in reader mode, the skin care device can read data from an external tag. In doing so, data received from the tag by the skin care device may be coded in NFC Data Exchange Format determined by NFC forum. Moreover, the NFC forum provides 4 record types. Particularly, the NFC forum provides 4 Record Type Definitions (RTD) such as a smart poster, a text, a Uniform Resource Identifier (URI), a general control and the like.

In case that the NFC module operates in Peer-to-Peer (P2P) mode, the skin care device 100 can perform P2P communication with another device. In this case, Logical Link Control Protocol (LLCP) is applicable to the P2P communication. For the P2P communication, connection may be created between the skin care device 100 and another external terminal. The created connection may be classified into a connectionless mode of exchanging 1 packet and then ending or a connection-oriented mode of consecutively exchanging packets. Through P2P communication, data, setup parameters for Bluetooth/Wi-Fi connection and the like may be exchanged. Yet, since an available distance of NFC communication is short, the P2P mode may be effectively utilized in exchanging data in small size.

The location information module 113 is a module generally configured to obtain a location (or current location) of the skin care device 100. Representatively, the location information module 113 may include a Global Position System (GPS) module, a Wireless-Fidelity (Wi-Fi) module, or both. As one example, when the skin care device 100 uses a GPS module, a location of the skin care device 100 can be acquired using a signal sent from a GPS satellite. As another example, when the skin care device uses the Wi-Fi module, a location of the skin care device 100 can be acquired based on information related to a wireless Access Point (AP) that transmits/receives a wireless signal to/from the Wi-Fi module. If desired, the location information module 113 may alternatively or additionally function with any of the other modules of the wireless communication unit 110 to obtain data related to the location of the skin care device 100. The location information module 113 is a module used to obtain a location (or current location) of the skin care device 100, but is non-limited by a module for directly calculating or obtaining a location of the skin care device 100.

The input unit 120 may include a camera 121 or a video input unit for a video signal input and a user input unit 122 (e.g., a touch key, a push key, etc.) for receiving an input of information from a user. Image data collected by the input unit 120 may be analyzed and processed into a user's control command.

The camera 121 may process image frames of still pictures or video obtained by image sensors in video call mode or image capture mode. The processed image frames can be displayed on the display unit 141 or stored in the memory 160.

The camera 121 typically includes at least one a camera sensor (e.g., CCD, CMOS etc.), a photo sensor (or image sensor) and a laser sensor.

Implementing the camera 121 with a laser sensor may allow detection of a touch of a sensing target with respect to a 3D stereoscopic image. The photo sensor may be laminated on, or overlapped with, a display device. The photo sensor may be configured to scan movement of the sensing target in proximity to the touchscreen. In more detail, the photo sensor may include photo diodes and transistors in rows and columns to scan a content put on the photo sensor using an electrical signal which changes according to the quantity of light applied to the photo diode. Namely, the photo sensor may calculate the coordinates of the sensing target according to variation of light to thus obtain location information of the sensing target.

The camera 121 provided to the skin care device 100 may perform a function of photographing a skin surface condition particularly. In case that the display unit 141 is provided, a photographed skin surface condition is outputted thereto to enable a user to check the corresponding condition.

The user input unit 122 is a component configured to receive an input of information from a user. If information is inputted through the user input unit 122, the controller 170 can control an operation of the skin care device 100 to correspond to the inputted information. The user input unit 122 may include one or more of a mechanical input means (e.g., a mechanical key, e.g., a button located on a front and/or rear surface or a side surface of the skin care device 100, a dome switch, a jog wheel, a jog switch, etc.) and a touch-sensitive input means. As one example, the touch-sensitive input means may include a virtual key, a soft key or a visual key, which is displayed on a touchscreen through software processing, or a touch key which is disposed on a part other than the touchscreen. On the other hand, the virtual key or the visual key may be displayed on the touchscreen in various shapes, e.g., graphic, text, icon, video, or a combination thereof.

The sensing unit 140 may include one or more sensors for sensing at least one of information in the skin care device 100, surrounding environment information of the skin care device 100 and user information. For example, the sensing unit 130 may include at least one of a proximity sensor 131, an illumination sensor 132, a touch sensor, an acceleration sensor, a magnetic sensor, a G-sensor, a gyroscope sensor, a motion sensor 133, an RGB sensor, an infrared (IR) sensor, a finger scan sensor, a ultrasonic sensor, an optical sensor (e.g., camera 121), a microphone, a battery gauge, an environment sensor (e.g., a barometer, a hygrometer, a thermometer, a radiation detection sensor, a thermal sensor, and a gas sensor, etc.), and a chemical sensor (e.g., an electronic nose, a health care sensor, a biometric sensor, and the like), to name a few. Meanwhile, the skin care device 100 disclosed in the present specification may combine to utilize information obtained from at least two of the above sensors.

The sensing unit 130 senses at least one of information in the skin care device 100, surrounding environment information of the skin care device 100 and user information and generates a sensing signal corresponding to the sensed information. Based on such a sensing signal, the controller 170 can control a drive or operation of the skin care device 100 or perform a data processing, function or operation related to an application program installed on the skin care device 100.

The proximity sensor 131 may include a sensor configured to sense presence or absence of an object approaching a prescribed detection surface or an object located nearby using an electromagnetic field, infrared rays, or the like without a mechanical contact. The proximity sensor 131 may be disposed in an inner area of the skin care device 100 enclosed by the above-mentioned touchscreen or near the touchscreen.

The proximity sensor 131, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touchscreen is implemented as a capacitance type, the proximity sensor 131 can be configured to sense proximity of an object by changes of an electromagnetic field, which is responsive to an approach of the object with conductivity. In this case, the touchscreen (or a touch sensor) may also be categorized as a proximity sensor.

For clarity of description, the term "proximity touch" will often be referred to herein to denote the scenario in which an object is positioned to be proximate to the touchscreen without contacting the touchscreen. The term "contact touch" will often be referred to herein to denote the scenario in which an object makes physical contact with the touchscreen. For the position corresponding to the proximity touch of the pointer relative to the touchscreen, such position will correspond to a position where the pointer is vertical to the touchscreen. The proximity sensor 131 may sense proximity touch, and proximity touch patterns (e.g., proximity touch distance, proximity touch direction, proximity touch speed, proximity touch time, proximity touch position, proximity touch moving status, etc.). Meanwhile, the controller 170 processes data (or information) corresponding to proximity touches and proximity touch patterns sensed by the proximity sensor 131, and is able to output visual information corresponding to the processed data to the touchscreen. Furthermore, the controller 170 can control the skin care device 100 to execute different operations or process different data (or information) according to whether a touch to a same point on the touchscreen is a proximity touch or a contact touch.

A touch sensor can sense a touch (or a touch input) applied to the touchscreen (or the display unit 141) using at least one of a variety of touch types such as a resistive type, a capacitive type, an infrared type, an ultrasonic type, a magnetic field type, etc.

For example, the touch sensor may be configured to convert changes of pressure applied to a specific part of the touchscreen, or convert capacitance occurring at a specific part of the touchscreen, into electric input signals. The touch sensor may also be configured to sense not only a touched position and a touched area, but also touch pressure and/or touch capacitance. Here, the touch object is generally used to apply a touch input to the touch sensor. Examples of typical touch objects include a finger, a touch pen, a stylus pen, a pointer, and the like.

The controller 170 may execute the same or different controls according to a type of a touch object that touches the touchscreen (or a touch key provided in addition to the touchscreen). Whether to execute the same or different control according to the type of the touch object may be determined based on a current operating state of the skin care device 100 or a currently executed application program.

In some embodiments, the above-described touch sensor and the above-described proximity sensor may be implemented individually, or in combination, to sense various types of touches. Such touches to the touchscreen may include a short (or tap) touch, a long touch, a multi-touch, a drag touch, a flick touch, a pinch-in touch, a pinch-out touch, a swipe touch, a hovering touch, and the like.

An ultrasonic sensor may be implemented to recognize position information relating to a touch object using ultrasonic waves. Meanwhile, the controller 170 may calculate a position of a wave generation source based on information sensed by an illumination sensor and a plurality of ultrasonic sensors. Since light is much faster than ultrasonic waves, the time taken for the light to reach the optical sensor is much shorter than the time taken for the ultrasonic wave to reach the ultrasonic sensor. The position of the wave generation source may be calculated using this fact. Particularly, the position of the wave generation source can be calculated using a time difference from an ultrasonic wave arriving time by taking the light as a reference signal.

Thus, when there is a touch input to a touch sensor, signal(s) corresponding to the touch input can be sent to a touch controller. The touch controller may process the signal(s) and then transmit corresponding data to the controller 170. Eventually, the controller 170 can be aware that which region of the display unit 141 has been touched. Here, the touch controller may include a component separate from the controller 170 or the controller 170 itself.

The output unit 140 is configured to generate outputs related to vision, hearing and tactile sensation and may include at least one of a display unit 141, an audio output unit 142, a haptic module 143, and an optical output unit 144. The display unit 141 may have an inter-layered structure or an integrated structure with a touch sensor, thereby implementing a touchscreen. The touchscreen may provide an output interface between the skin care device 100 and a user, as well as function as the user input unit 122 that provides an input interface between the skin care device 100 and the user.

The display unit 141 displays (or outputs) information processed in the skin care device 100. For example, the display unit 141 may display execution screen information of an application program launched on the skin care device 100 or User Interface (UI) or Graphic User Interface (GUI) information according to the execution screen information.

The interface unit 150 serves as a passage to various types of external devices connected to the skin care device 100. The interface unit 150 may include any of wired or wireless ports, external power supply ports, wired or wireless data ports, memory card ports, ports for connecting a device having an identification module, and the like. The skin care device 100 may perform assorted control functions associated with a connected external device, in response to a case that an external device is connected to the interface unit 150.

The memory 160 stores data supportive of various functions of the skin care device 100. The memory 160 may store a multitude of application programs (or applications) executed on the skin care device 100 and data for operations of the skin care device 100. Some of the application programs may be downloaded from an external server via wireless communication. At least one portion of the application programs may be installed on the skin care device 100 at the time of manufacturing or shipping, which is typically the case for basic functions of the skin care device 100. It is common for application programs to be stored in the memory 160, installed on the skin care device 100, and executed by the controller 170 so as to perform an operation (or function) of the skin care device 100.

The controller 170 typically functions to control overall operations of the skin care device 100, in addition to the operations associated with the application programs. The controller 170 may provide or process information or functions appropriate for a user by processing signals, data, information and the like, which are input or output by the various components described above, or launching application programs stored in the memory 160.

In order to launch an application program stored in the memory 160, the controller 170 can control some or all of the components illustrated in FIG. 1. Moreover, in order to launch the application program, the controller 170 may activate at least two of the components included in the skin care device 100 by combing them together.

Under the control of the controller 170, the power supply unit 180 receives external power or internal power, thereby supplying to the components included in the skin care device 100. The power supply unit 180 may include a battery, and the battery may include a built-in battery or a replaceable battery.

At least some of the above-mentioned components can cooperatively operate to implement operations, controls or controlling methods of the skin care device. And, the operations, controls and controlling methods of the skin care device can be implemented on the skin care device by running at least one application program stored in the memory 160.

Figure 2:
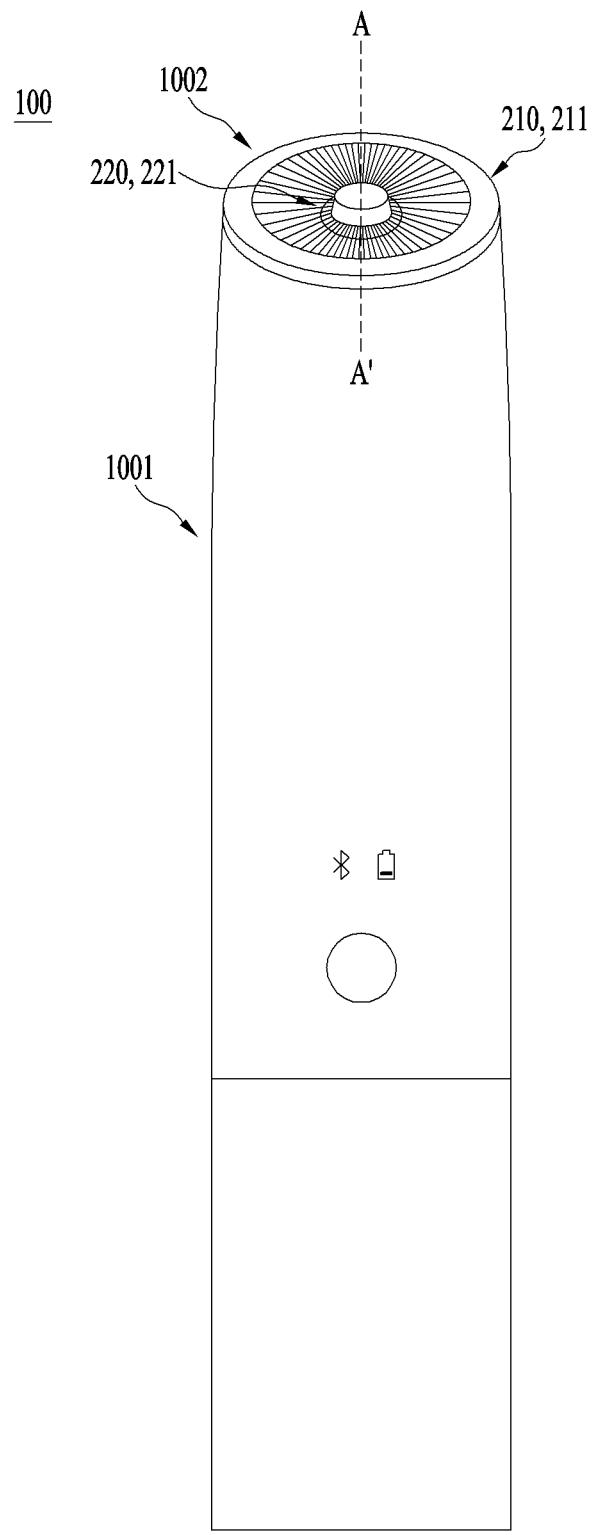
FIG. 2 is a front diagram of a skin care device related to the present invention.

FIG. 2 is a front diagram of a skin care device 100 related to the present invention.

The present invention is capable of a skin care according to optical and thermal energy transfer types among the aforementioned various skin care types. For clarity of description, the former and the latter shall be referred to as an optical care and a thermal care, respectively.

A heating unit 210 for a thermal care and a light source unit 220 for an optical care may be provided to one end of a housing 1001.

The heating unit 210 or the light source unit 220 may come in contact with a user's skin through a first face 1002 of one end of the housing 1001.

A heat transfer bracket 211 in the heating unit 210 plays a role in transferring heat by directly contacting with a user's skin. The heat transfer bracket 211 may be provided along an outer rim of one end of the housing 1001.

A light transfer bracket 221 forms a path for applying a light projected from the light source unit 220 to a user's skin through the light transfer bracket 221. The light transfer bracket 221 may form an inside area of the heat transfer bracket 211.

Figure 3:
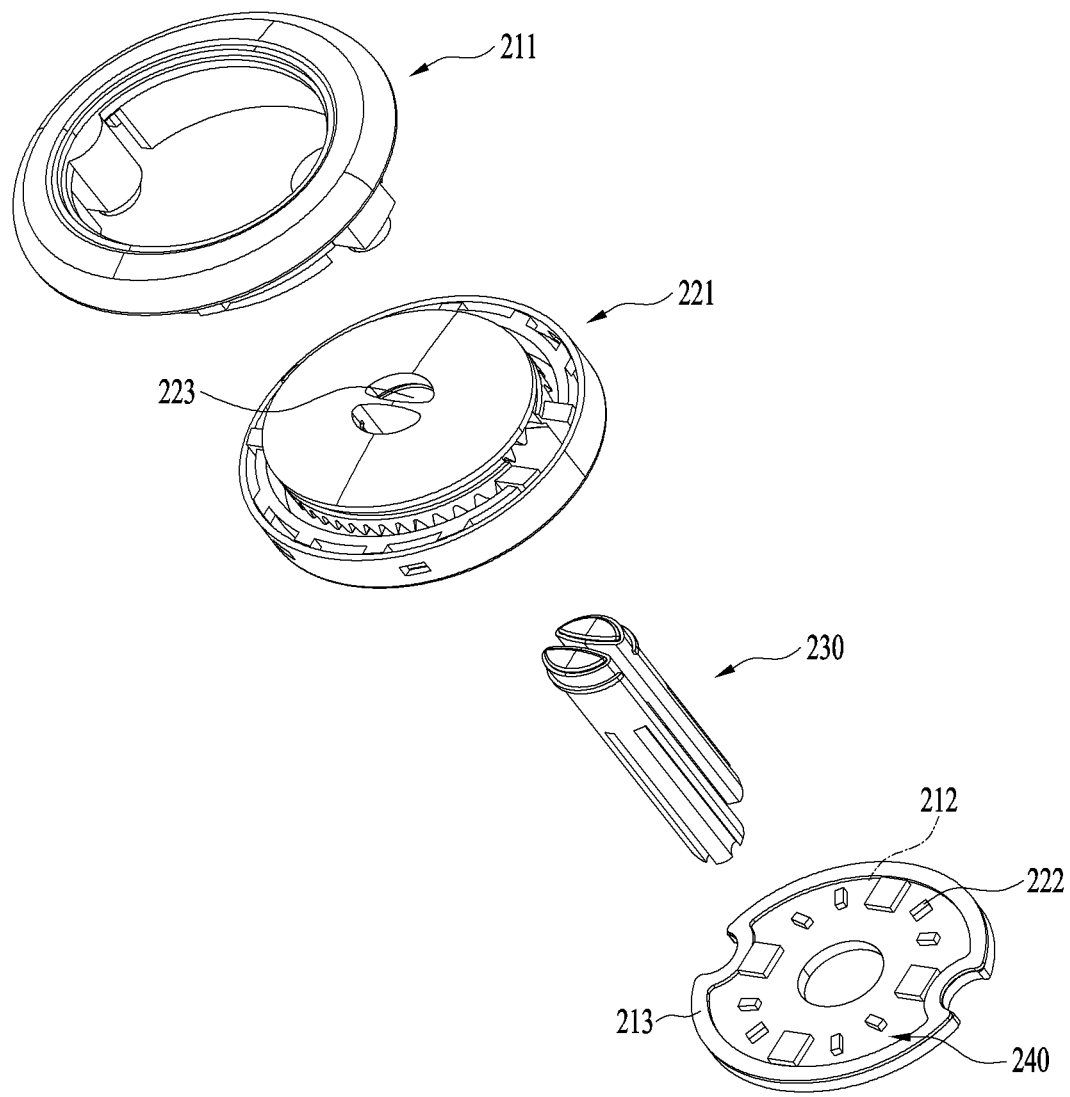
FIG. 3 is a partially-exploded perspective diagram of a skin care device related to the present invention.

FIG. 3 is a partially-exploded perspective diagram of a skin care device 100 related to the present invention.

A heat transfer path to a heat transfer bracket 211 is described as follows. Thermal energy may be generated through a heating pad 213 provided to a first board 240. Electric energy is converted into thermal energy by the heating pad 213 of the first board 240.

The generated thermal energy is transferred to the heat transfer bracket 211.

A temperature sensor 212 provided to a skin care device 100 can measure a temperature state of the skin care device 100. Since parts of the device may be damaged by the generated thermal energy or excessive heat is transferred to a user so as to possibly damage a user's skin, an accurate temperature measurement is required.

The temperature sensor 212 may be provided to a backside of the first board 240. The temperature sensor 212 makes it a rule to measure a temperature of the heat transfer bracket 211 by avoiding an area of the first board 240 having the heating pad 213 provided thereto. The reason for this is to accurately obtain a temperature applied to a user by obtaining a substantially applied temperature of the thermal care.

A light source 222 configured to project light in the light source unit 220 may be provided within the light transfer bracket 221.

As a first hole 223 is formed at the center of the light transfer bracket 221, at least one portion of a skin measurement sensor 230 may be provided in a manner of being projected through the first hole 223. The skin measurement sensor 230 may commonly refer to a sensor configured to measure a state of a skin by coming in contact with the skin.

One example of the skin measurement sensor 230 may include a Bioelectric Impedance Analysis (BIA) sensor.

The BIA sensor measures total body water, fat mass and the like by measuring resistance.

By receiving feedback of the skin care device 100 through the total body water, the fat mass and the like measured by the skin measurement sensor 230, management suitable for the feedback can be performed. For example, a drive time of each of the thermal care and the optical care may be adjusted, or a driven time ratio between the terminal care and the optical care and mutual patterns can be adjusted.

Or, a user can enable the heating unit 210 or the light source unit 220 manually and selectively on the basis of the result of the skin measurement sensor 230, or control the controller 170 to enable both of the configurations simultaneously.

Figure 4:
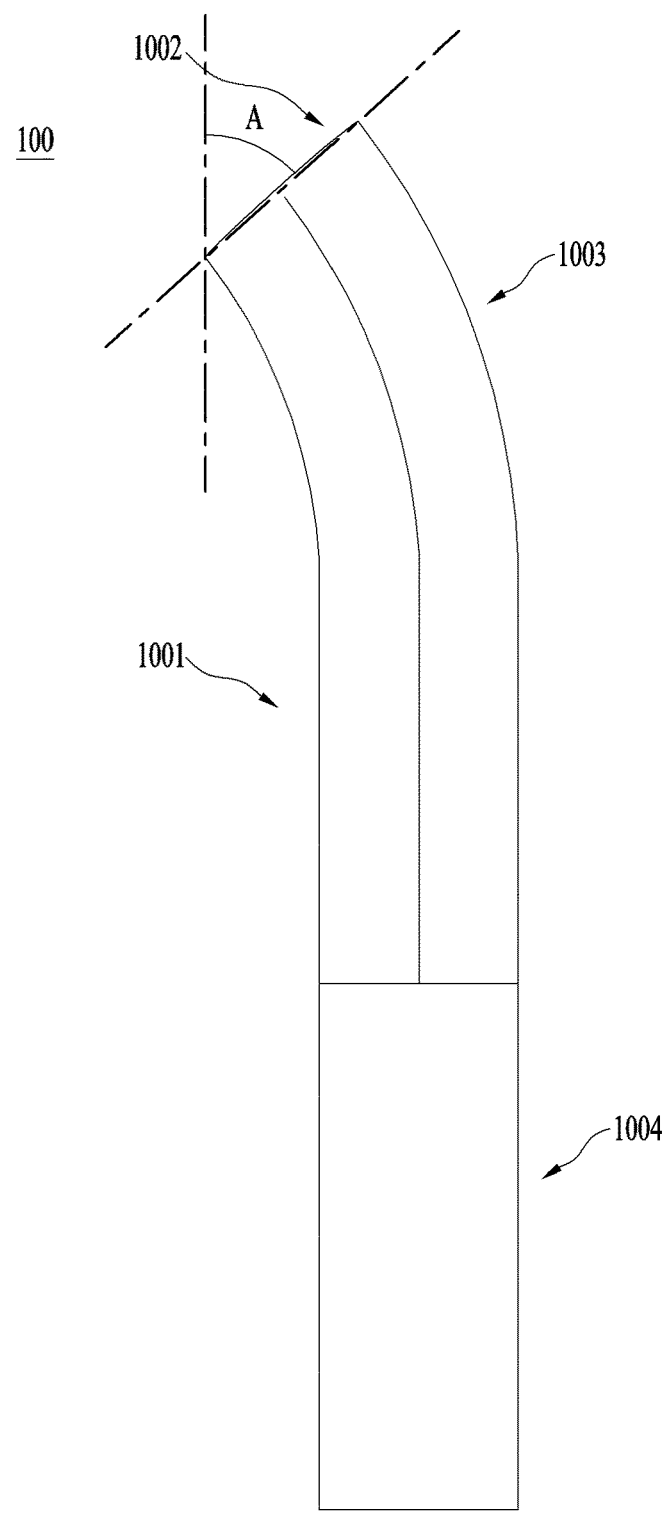
FIG. 4 is a side-view diagram of a skin care device related to the present invention.

FIG. 4 is a side-view diagram of a skin care device 100 related to the present invention.

The above-described components are installed/provided in/to a housing 1001 of the skin care device 100.

The housing 1001 may have a curved portion 1003 configured in a manner that one end of the housing 1001 is curved in one lateral direction including a front direction.

As one end of the housing 1001 is curved with reference to a length direction of a grip part 1004 held with a user's hand, a first face 1002 can incline at A° with reference to the length direction of the grip part 1004.

Particularly, the A° may include 45°.

The user can sufficiently use the skin care device 100 in a suitable area below a face by holding the grip part 1004 of the skin care device 100 without stretching out a user's hand.

Figure 5:
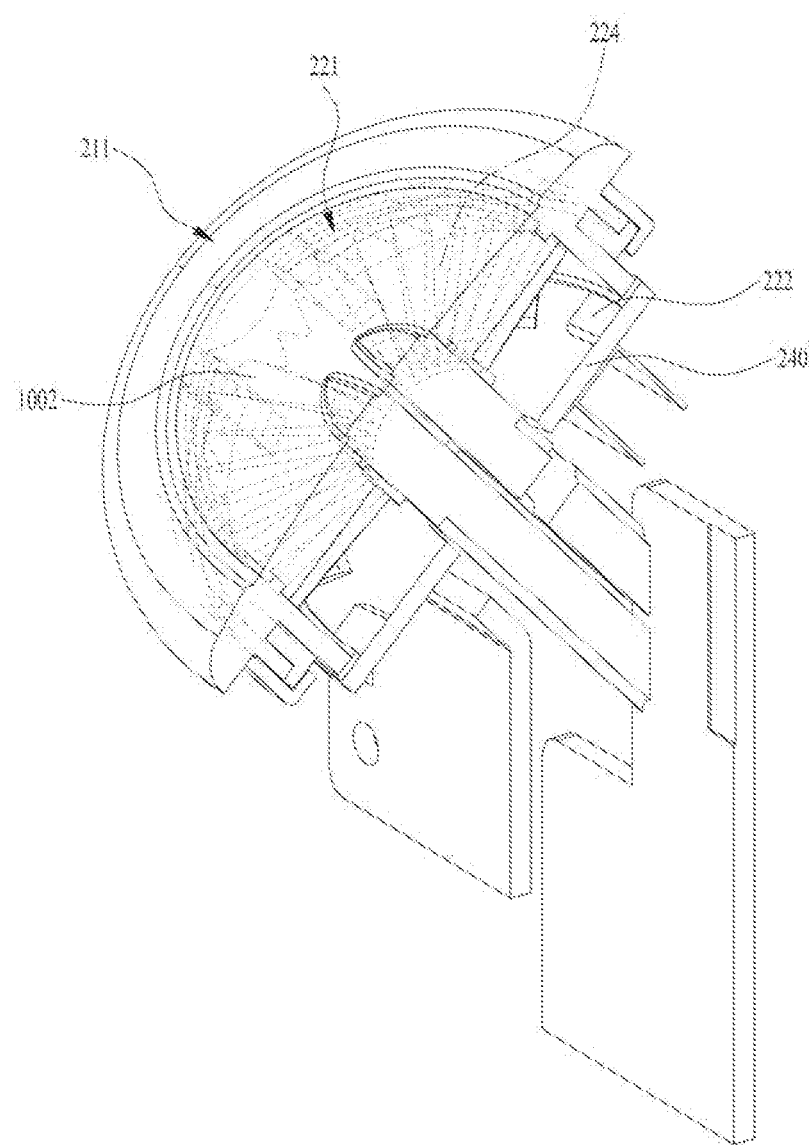
FIG. 5 shows a portion of a cross-sectional diagram along a direction A-A' in FIG. 2.

FIG. 5 shows a portion of a cross-sectional diagram along a direction A-A' in FIG. 2.

A structure for an optical care including the light source 222 can be installed in the light transfer bracket 221. The light source 222 is mounted on the first board 240 so as to project light. The light projected from the light source 222 can be projected out of the first face 1002 of the skin care device 100 through the light transfer bracket 221.

The light transfer bracket 221 may include a light transmissive material. For example, the light transfer bracket 221 may include a plastic material such as transparent or semi-transparent poly-carbonate.

An inner lateral side of the light transfer bracket 221 may have a light guide part 224 inside so as to minimize optical energy lost in a manner that light is projected out of the first face 1002 instead of being reflected inward.

The light guide part 224 is formed in comb pattern that spreads in fan shape so as to enable the projected light to spread in all directions.

Figure 6:
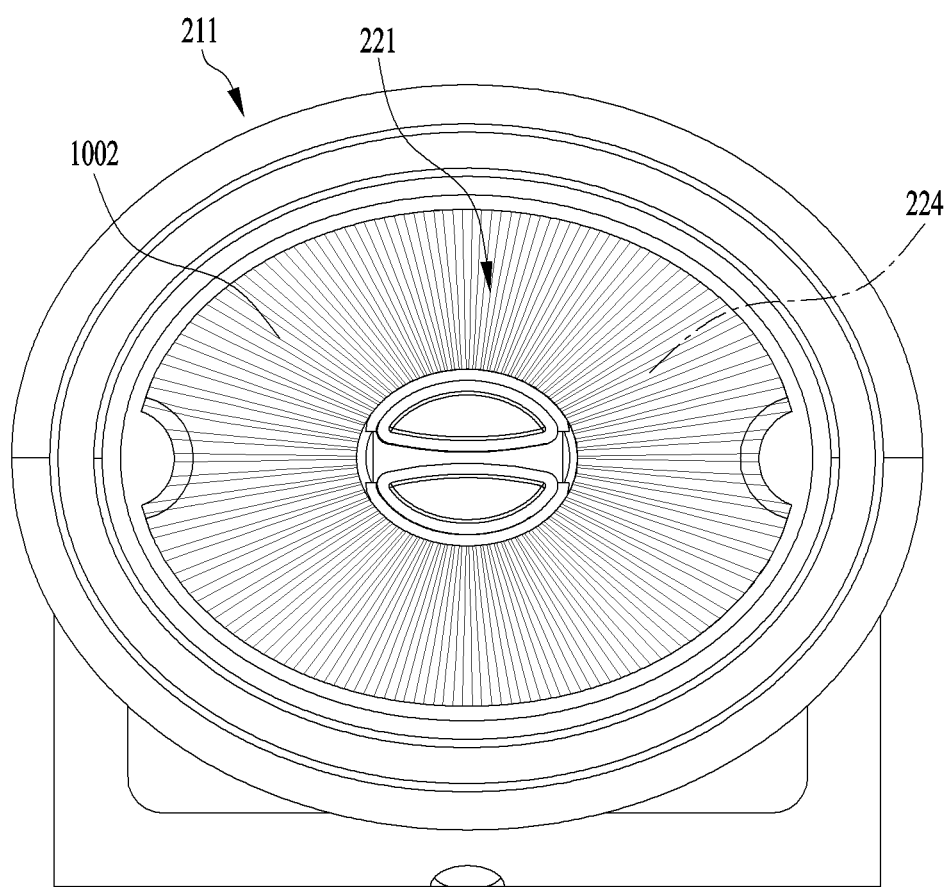
FIG. 6 shows a portion of a skin care device related to the present invention, viewed in a first face.

FIG. 6 shows a portion of the skin care device 100 related to the present invention, viewed in the first face 1002.

An incline pattern is formed in a comb pattern spreading evenly outward from a center when the first face 1002 is looked straight, whereby the projected light can arrive in a wider area instead of being limited to the first face 1002.

Figure 7:
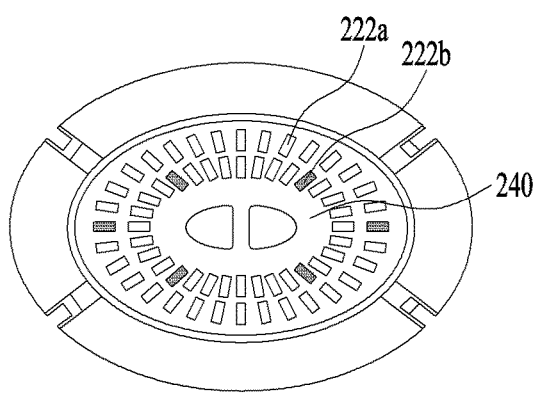
FIGS. 7(a) to 7(d) shows several embodiments for light source deployment of a skin care device related to the present invention.
Figure 7:
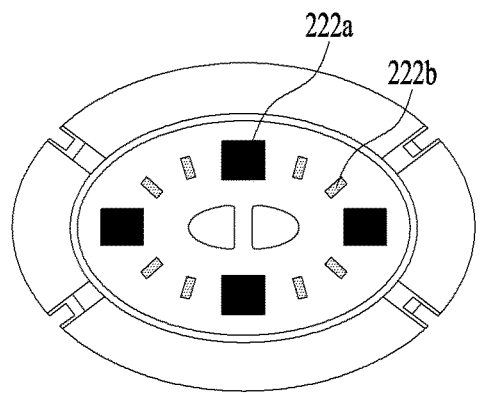
Figure 7:
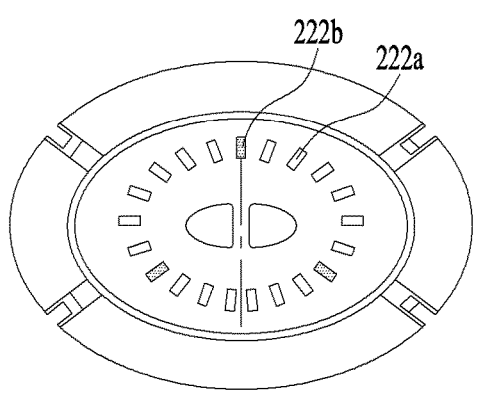
Figure 7:
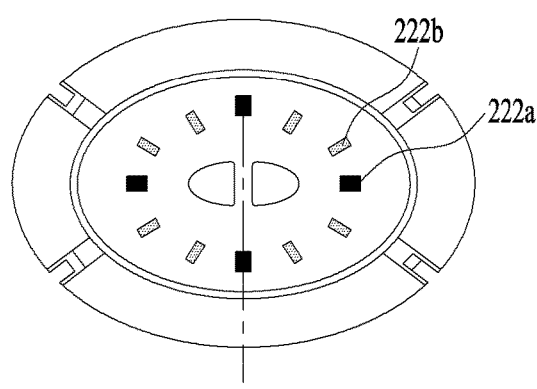

FIGS. 7(*a*) to 7(*d*) shows several embodiments for deployment of a light source 222 of a skin care device 100 related to the present invention.

A light source 222 of a light source unit 220 may include a plurality of light sources 222 differing from each other in wavelength, thereby bringing various effects.

Particularly, according to the present embodiment, a complex light source unit 220 having two kinds of wavelength ranges of a red light source and a near-infrared light source. The red light source and the near-infrared light source can be characterized in having a wavelength ranging between 630~670 nm and a wavelength ranging between 800~1,000 nm, respectively.

The red light source has skin care and treatment effects of inflammation cure, UV resistance and the like, and the near-infrared light source has effects of skin scar prevention, pigmentation prevention and the like.

The present embodiment takes an example that a red light source and a near-infrared light source are provided, by which the present invention is non-limited. If necessary, a light source 222 of a different wavelength range or a light source 222 of three or more wavelength ranges can be provided.

As the minimum number of the red light sources and the near-infrared light sources are provided, it is able to consider the deployment and number of the light sources capable of transferring the maximum energy.

As a result of simulation, it is observed that a case [FIG. 7(*b*)] of 4 first light source units 222*a* of a red light source and 8 second light source units 222*b* of a near-infrared light source generates the most efficient energy. Particularly, a circular pattern can be provided in a manner that 2 of the 8 second light source units 222*b* are disposed in each of 4 spaces respectively provided by 2 neighboring first light source units 222*a* among the 4 first light source units 222*a* with the same diameter.

It is unnecessary to relatively specify a wavelength range. In some cases, light sources of various wavelength ranges can be provided. A light source generating relatively high energy and a light source generating relatively low energy can be generalized into the first light source unit 222*a* and the second light source unit 222*b*, respectively.

The controller 170 can control voltage to be applied to the first light source unit 222*a* and the second light source unit 222*b* selectively or simultaneously.

Figure 8:
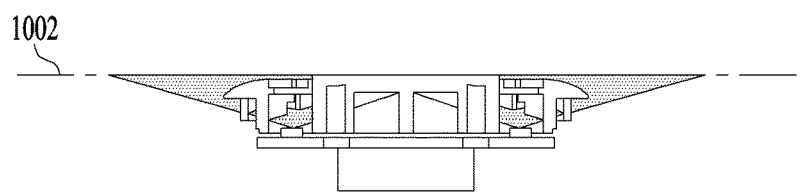
FIG. 8(a) and FIG. 8(b) show a light source projected area viewed from a first face in association with a skin care device of the present invention.
Figure 8:
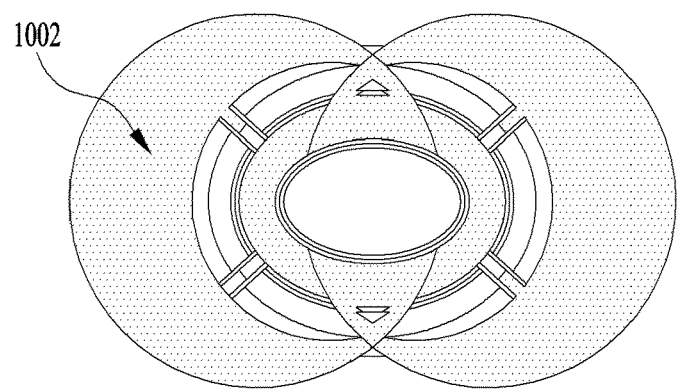
Figure 8:
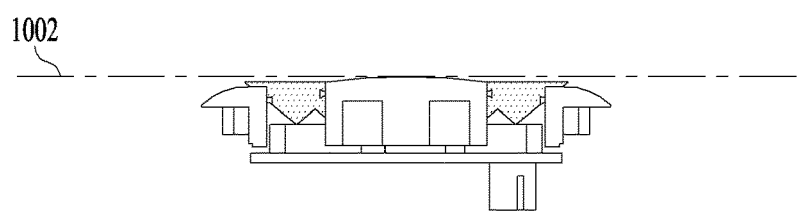
Figure 8:
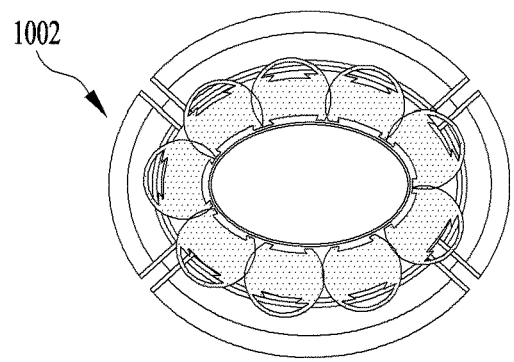

FIG. 8(*a*) and FIG. 8(*b*) show a light source projected area of the light source 222 viewed from the first face 1002 in association with the skin care device 100 of the present invention.

FIG. 8(a) shows an area reached by the red light source of the light source unit 220 deployed in FIG. 7(b), and FIG. 8(b) shows an area reached by the light source 222 projected by the near-infrared light source of the light source unit 220 deployed in FIG. 7(b).

It is observed that the light source 222 affects a skin area relatively wide in comparison with the rest of the comparative group shown in FIG. 7(a), FIG. 7(b) and FIG. 7(c).

Figure 9:
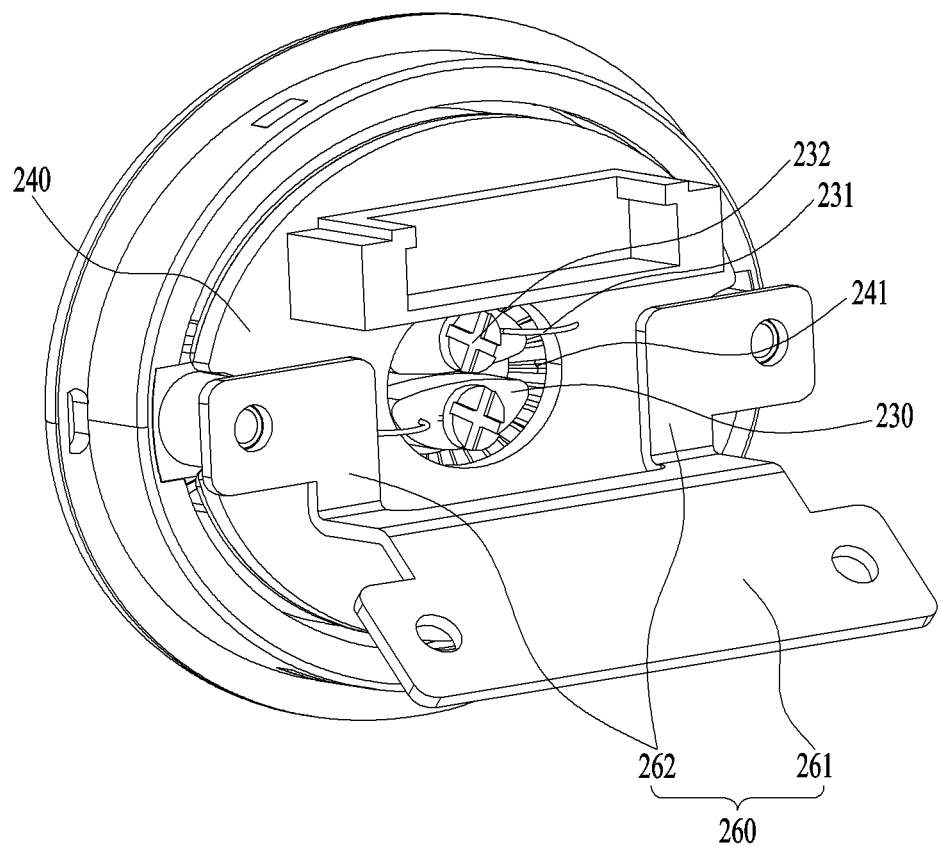
FIG. 9 is a perspective diagram of a partial rear side of a skin care device of the present invention.

FIG. 9 is a perspective diagram of a partial rear side of the skin care device 100 of the present invention.

The skin measurement sensor 230 can function by being electrically connected to the first board 240. Nonetheless, if the skin measurement sensor 230 is mounted on the first board 240 in a manner of directly touching the first board 240, heat generated from the first board 240 is directly transferred to the skin measurement sensor 230 so as to possibly make a noise and cause bad influence to the component durability.

Therefore, it is necessary to provide a structure of preventing the heat, which is generated from the first board 240 by the heating unit 210 and the light source unit 220, from being transferred to the skin measurement sensor 230.

One inner end of the skin measurement sensor 230 can be provided by being physically spaced apart from the first board 240. Such a spaced structure can minimize an effect that the heat generated from the first board 240 is transferred to the skin measurement sensor 230.

The skin measurement sensor 230 can be fixed by being fitted into the first hole 223 of the light transfer bracket 221 instead of being fixed to the first board 240 like FIG. 2. The skin measurement sensor 230 can be electrically connected to the first board 240 through a connection wire 231.

The connection wire 231 may be connected to one end surface of the skin measurement sensor 230, pass through a second hole 241 formed in the first board 240, and then joined to a backside of the first board 240. The connection wire 231 may be fixed to the skin measurement sensor 230 through a fixing screw 232.

Figure 10:
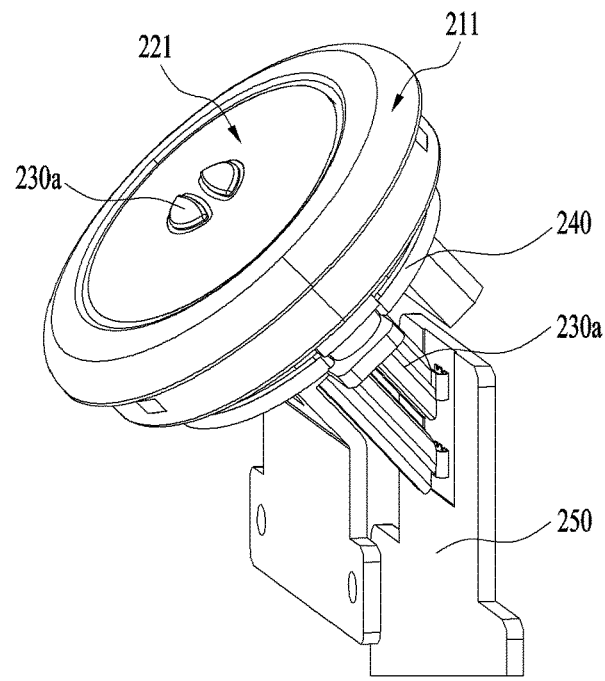
FIG. 10(a) and FIG. 10(b) show one embodiment of a skin care device related to the present invention.
Figure 10:
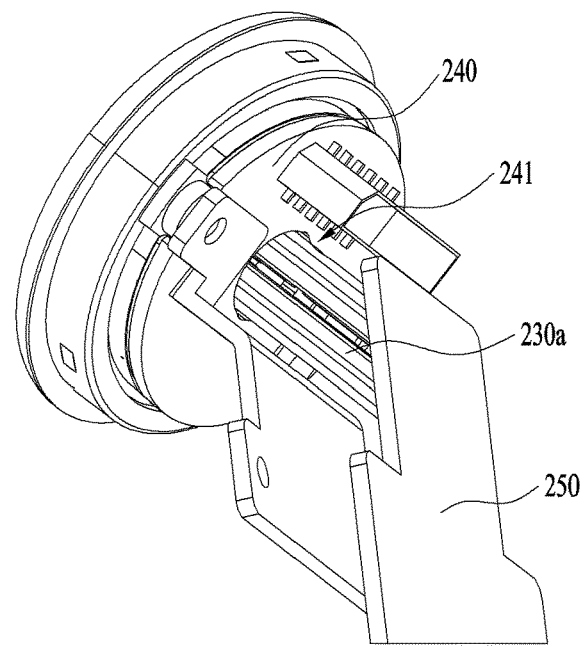

FIG. 10(a) and FIG. 10(b) show one embodiment of the skin care device related to the present invention.

As an embodiment of another type of preventing the first board 240 and the skin measurement sensor 230 from coming in contact with each other, the skin measurement sensor 230 may be mounted not on the first board 240 but on the second board 250.

The skin measurement sensor 230 may pass through the second hole 241 of the first board 240 so as to be joined to the second board 250. The present embodiment may have a configuration of a skin measurement sensor 230a having a relatively increased length in comparison with the embodiment of FIG. 9.

The second board 250 may have a structure that electronic parts are mounted thereon and play a role similar to that of the first board 240.

Figure 11:
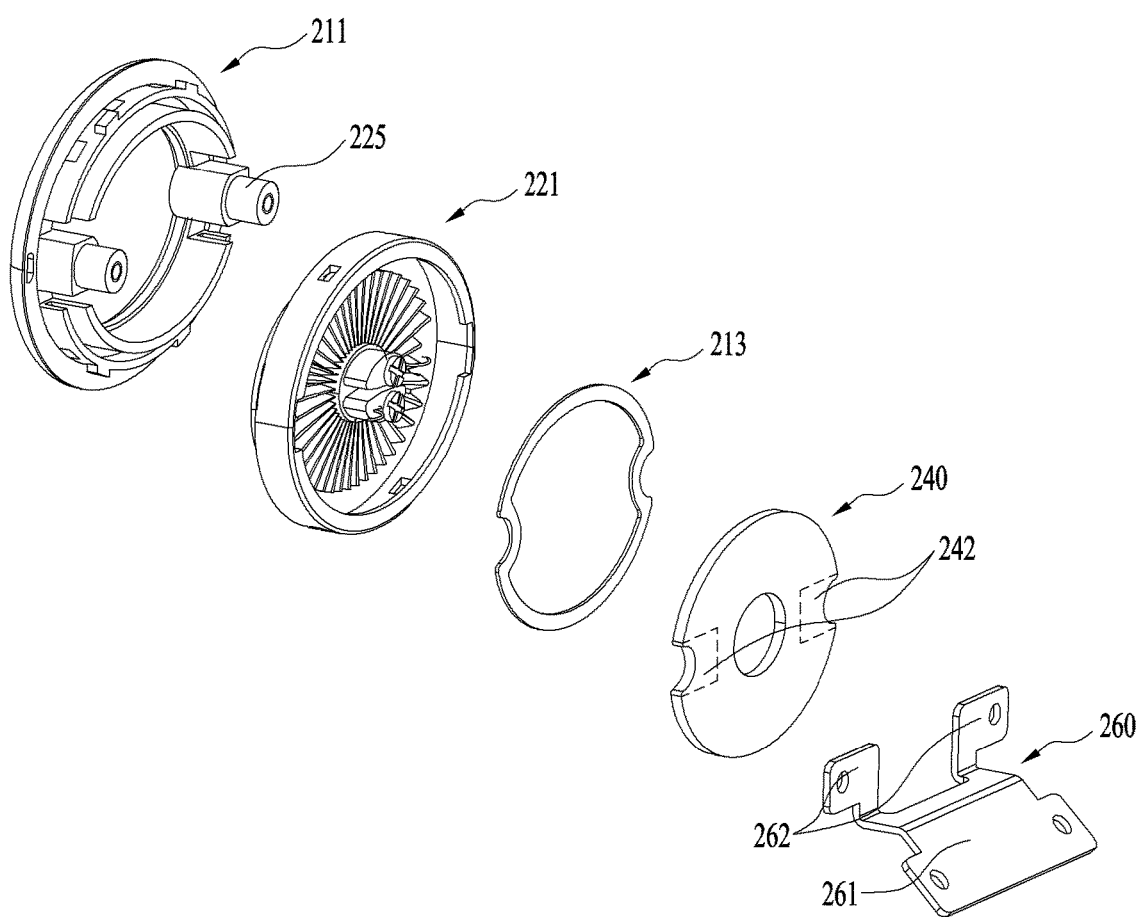
FIG. 11 is a perspective diagram of a rear side of a partially exploded skin care device related to the present invention.

FIG. 11 is a perspective diagram of a rear side of a partially exploded skin care device 100 related to the present invention.

As described above, the temperature of the skin care device is raised due to the heating pad 213 for the thermal care, the activation of the light source 222 for the optical care, etc.

The temperature increase of the heating pad 213 for the thermal care is necessary but the heat generated from the activation of the light source 222 for the optical care becomes an unintended heating.

Moreover, in case of the temperature increase for the thermal care, it is necessary to prevent an unnecessary overheating or a heater transfer to an unnecessary area.

A heat radiation part 260 having a heat radiation plate 261 can play a role in radiating the heat generated from the first board 240, and more particularly from the light source 222.

A heat radiation terminal 262 of the heat radiation part 260 is fixed to a joining portion 225 of the heat transfer bracket 211 and comes in contact with a heat radiation contact portion 242 of the first board 240, thereby playing a role in transferring the heat generated from the first board 240 to the heat radiation plate 261.

The temperature of the first board 240 is mainly raised by the red light source of the light source unit 220 in particular. As the red light source has a short wavelength, it produces relatively high energy. Therefore, the heat radiation contact portion is provided near a backside of a red light source located point, thereby radiating heat most efficiently.

Thus, in case that the red light source is configured as shown in the embodiment of FIG. 7(b), the heat radiation contact portion 242 can be provided to each of both ends of the first board 240.

Yet, it is not mandatory for the heat radiation contact portion to be provided to an area corresponding to the red light source. The heat radiation contact portion 242 may be formed in an area corresponding to the first light source unit 222a of the wavelength range on which heat of relatively high temperature is generated.

Since the heat radiation terminal 262 can be provided only to a partial area of a whole area of the first board 240 due to the limited space occupied by the circuit of the first board 240 and the like, the heat radiation plate 261 is provided in a size greater than that of the heat radiation terminal 262, thereby efficiently radiating the heat transferred from the heat radiation terminal 262.

As the aforementioned heating part 213 is provided to the first board 240 in a manner of avoiding the contact with the joining portion 225 of the heat transfer bracket 211 or the heat radiation terminal 262, the heating path to the heat transfer bracket 211 for the terminal care and the heat radiation path of the heat generation due to the optical care can be separated from each other as far as possible.

The heat radiation plate 261 is provided in a direction corresponding to the shape of the housing 1001 having the curved portion 1003 shown in FIG. 4, it can have a size as large as possible. Namely, the heat radiation plate 261 may be inclined to the first board 240.

Those skilled in the art will appreciate that the present disclosure may be carried out in other specific ways than those set forth herein without departing from the spirit and essential characteristics of the present disclosure.

The above embodiments are therefore to be construed in all aspects as illustrative and not restrictive. The scope of the disclosure should be determined by the appended claims and their legal equivalents, not by the above description, and all changes coming within the meaning and equivalency range of the appended claims are intended to be embraced therein.

MODE FOR INVENTION

Various modes for the implementation of the invention are described in BEST MODE FOR INVENTION for the implementation of the invention.

The above description is to be construed in all aspects as illustrative and not restrictive. The scope of the disclosure should be determined by the appended claims and their legal equivalents, not by the above description, and all changes coming within the meaning and equivalency range of the appended claims are intended to be embraced therein.

INDUSTRIAL APPLICABILITY

As described above, the present invention is applicable to all skin care devices entirely or in part.

What is claimed is:

1. A skin care device, comprising:
   a housing forming an exterior;
   a heat transfer bracket provided to one end of the housing;
   a light source unit installed at the one end of the housing;
   a light transfer bracket including a light-transmissive material, the light transfer bracket covering the light source unit by being fixed to the housing and having a first hole;
   a skin measurement sensor sensing at least one of total body water or fat mass and externally projected by passing through the first hole; and
   a first board having the light source unit mounted thereon, the first board spaced apart from the skin measurement sensor.

2. The skin care device of claim 1, wherein the skin measurement sensor includes a Bioelectric Impedance Analysis (BIA) sensor.

3. The skin care device of claim 1, further comprising a connection wire electrically connected to the skin measurement sensor and the first board through a second hole formed in the first board.

4. The skin care device of claim 1, further comprising a second board having the skin measurement sensor mounted thereon,
   wherein the skin measurement sensor passes through a second hole formed in the first board.

5. The skin care device of claim 1, further comprising:
   a conductive heat radiation contact portion provided to both sides of the first board; and
   a heat radiation part including a heat radiation plate inclined to the first board and a heat radiation terminal coming in contact with the conductive heat radiation contact portion by diverging from the heat radiation plate.

6. The skin care device of claim 5, wherein the light source unit includes a first light source unit corresponding to a red visible light range and wherein the conductive heat radiation contact portion is provided to an area corresponding to the first light source unit.

7. The skin care device of claim 1, wherein the heat transfer bracket forms a rim area of the one end of the housing, and
   wherein the light transfer bracket is formed in an inside area of the heat transfer bracket.

8. The skin care device of claim 7, wherein a comb pattern is formed on an inner lateral side of the light transfer bracket.

9. The skin care device of claim 1, the light source unit comprising:
   4 first light source units corresponding to a red visible light range; and
   8 second light source units corresponding to a near-infrared range,
   wherein the 4 first light source units are arranged in a circular form on the first board, and
   wherein every 2 of the 8 second light source units are arranged in each space between the first light source units along the circular form.

10. The skin care device of claim 9, further comprising a controller controlling voltage to be applied to the 4 first light source units and the 8 second light source units selectively or simultaneously.

11. A skin care device, comprising:
    a housing forming an exterior;
    a heat transfer bracket provided to one end of the housing;
    a light source unit installed at the one end of the housing;
    a light transfer bracket including a light-transmissive material, the light transfer bracket covering the light source unit by being fixed to the housing and having a first hole;
    a skin measurement sensor externally projected by passing through the first hole;
    a first board having the light source unit mounted thereon, and the first board having a second hole; and
    a second board having a skin measurement sensor mounted thereon,
    wherein the skin measurement sensor passes through the second hole so as to be spaced apart from the first board.

12. A skin care device, comprising:
    a housing forming an exterior;
    a heat transfer bracket provided to one end of the housing;
    a light source unit installed at the one end of the housing;
    a light transfer bracket including a light-transmissive material, the light transfer bracket covering the light source unit by being fixed to the housing and having a first hole;
    a skin measurement sensor externally projected by passing through the first hole;
    a first board having the light source unit mounted thereon;
    a conductive heat radiation contact portion provided to both sides of the first board; and
    a heat radiation part including a heat radiation plate inclined to the first board and a heat radiation terminal coming in contact with the conductive heat radiation contact portion by diverging from the heat radiation plate.

13. The skin care device of claim 12, wherein the light source unit includes a first light source unit corresponding to a red visible light range, and
    wherein the conductive heat radiation contact portion is provided to an area corresponding to the first light source unit.

* * * * *